(12) United States Patent
Storck et al.

(10) Patent No.: US 7,371,893 B2
(45) Date of Patent: May 13, 2008

(54) PRODUCTION OF ALDEHYDES, CARBOXYLIC ACIDS AND/OR CARBOXYLIC ACID ANHYDRIDES BY MEANS OF CATALYSTS CONTAINING VANADIUM OXIDE, TITANIUM DIOXIDE, AND ANTIMONY OXIDE

(75) Inventors: Sebastian Storck, Mannheim (DE); Jürgen Zühlke, Speyer (DE); Samuel Neto, Dresden (DE); Frank Rosowski, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/557,791

(22) PCT Filed: May 21, 2004

(86) PCT No.: PCT/EP2004/005510

§ 371 (c)(1),
(2), (4) Date: Aug. 9, 2006

(87) PCT Pub. No.: WO2004/103943

PCT Pub. Date: Dec. 2, 2004

(65) Prior Publication Data

US 2007/0060758 A1    Mar. 15, 2007

(30) Foreign Application Priority Data

May 23, 2003   (DE) .............................. 103 23 461

(51) Int. Cl.
*C07C 51/16* (2006.01)
*C07D 307/89* (2006.01)
(52) U.S. Cl. ...................... 562/410; 549/249
(58) Field of Classification Search ............... 562/410; 549/249

See application file for complete search history.

(56) References Cited

U.S. PATENT DOCUMENTS

| 4,356,112 A | | 10/1982 | Nakanishi et al. |
| 4,855,457 A | * | 8/1989 | Ramzi et al. ............... 549/239 |
| 5,235,071 A | * | 8/1993 | Ueda et al. ................. 549/248 |
| 5,969,160 A | | 10/1999 | Lindström |
| 6,586,361 B1 | * | 7/2003 | Heidemann et al. ........ 502/353 |

FOREIGN PATENT DOCUMENTS

| DE | 2005 969 | 8/1971 |
| EP | 0 163 231 B1 | 12/1985 |
| EP | 0 522 871 B1 | 1/1993 |
| EP | 0 539 878 B1 | 5/1993 |
| EP | 0 676 400 B1 | 10/1995 |
| EP | 1 063 222 A1 | 12/2000 |

* cited by examiner

*Primary Examiner*—Yvonne Eyler
*Assistant Examiner*—M Louisa Lao
(74) *Attorney, Agent, or Firm*—Connolly Bove Lodge & Hutz, LLP

(57) ABSTRACT

A description is given of a process for preparing aldehydes, carboxylic acids and/or carboxylic anhydrides, in particular phthalic anhydride, in which a gaseous stream comprising an aromatic hydrocarbon and molecular oxygen is passed at elevated temperature over a bed of a first catalyst and a bed which is made up of a second catalyst having a higher activity than the first catalyst and is located downstream of the first catalyst in the flow direction of the gaseous stream, wherein the catalytically active composition of the first catalyst comprises at least vanadium oxide, titanium dioxide and antimony oxide and the ratio of vanadium, calculated as $V_2O_5$, to antimony, calculated as $Sb_2O_3$, in the first catalyst is from 3.5:1 to 5:1. The source of antimony oxide used for the first catalyst is preferably particulate antimony trioxide having a mean particle size of from 0.5 to 5 µm. The process allows the desired oxidation products to be obtained in high yield over longer periods of time.

15 Claims, 1 Drawing Sheet

Figure 1:
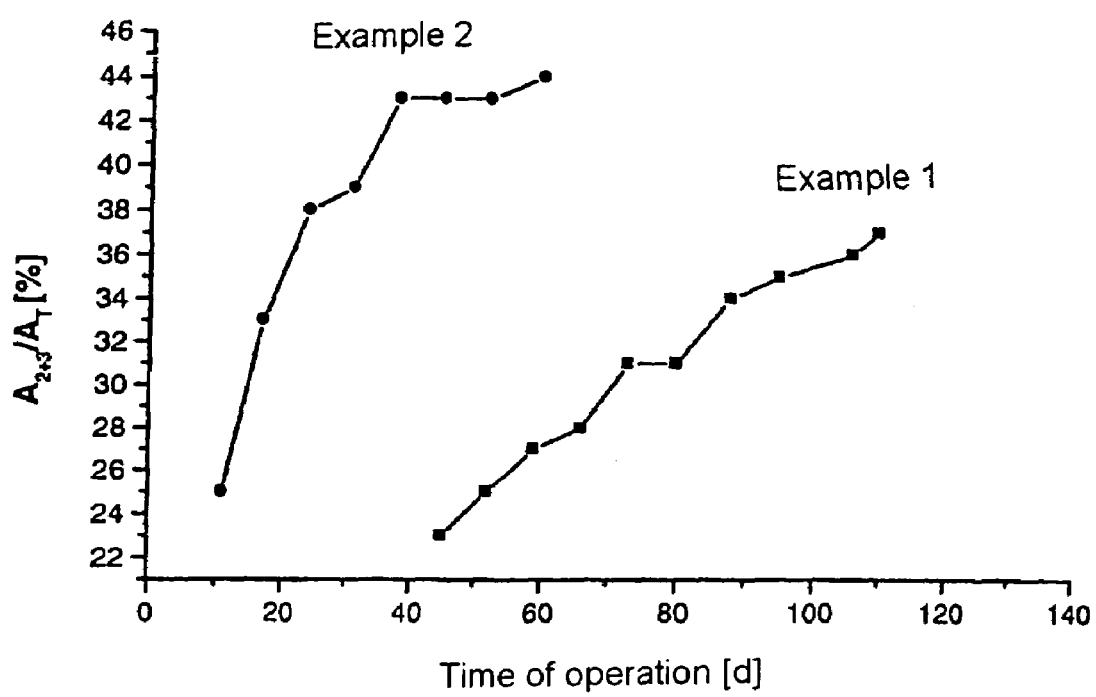

PRODUCTION OF ALDEHYDES, CARBOXYLIC ACIDS AND/OR CARBOXYLIC ACID ANHYDRIDES BY MEANS OF CATALYSTS CONTAINING VANADIUM OXIDE, TITANIUM DIOXIDE, AND ANTIMONY OXIDE

This application is a National Stage of PCT/EP2004/005510 filed May 21, 2004 which in turn claims priority from German Application 103 23 461.6, filed May 23, 2003.

The present invention relates to a process for preparing aldehydes, carboxylic acids and/or carboxylic anhydrides, in which a gaseous stream comprising an aromatic hydrocarbon and a gas comprising molecular oxygen is passed over a catalyst bed at elevated temperature.

Many aldehydes, carboxylic acids and/or carboxylic anhydrides are prepared industrially by catalytic gas-phase oxidation of aromatic hydrocarbons such as benzene, o-, m- or p-xylene, naphthalene, toluene or durene (1,2,4,5-tetramethylbenzene) in fixed-bed reactors, preferably shell-and-tube reactors. Depending on the starting material, these processes give, for example, benzaldehyde, benzoic acid, maleic anhydride, phthalic anhydride, isophthalic acid, terephthalic acid or pyromellitic anhydride. These processes predominantly use catalysts based on vanadium oxide and titanium dioxide.

The gas-phase oxidation is strongly exothermic. Local temperature maxima, known as hot spots, in which the temperature is higher than in the remainder of the catalyst bed occur. These hot spots give rise to secondary reactions such as the total combustion of the starting material or lead to formation of undesirable by-products which can be separated from the reaction product only with great difficulty, if at all. Furthermore, above a certain hot spot temperature, the catalyst can be irreversibly damaged.

To reduce the temperature of these hot spots, it has become common practice to arrange catalysts of differing activity in zones in the catalyst bed, with the less active catalyst being located toward the gas inlet and the more active catalyst being located toward the gas outlet.

EP-A 1 063 222 discloses a process for preparing phthalic anhydride by gas-phase oxidation over three or more catalyst zones. Catalysts are prepared from a slurry comprising, besides titanium dioxide and subordinate components, 121.86 g of ammonium metavanadate and 37.89 g of antimony trioxide or 96.48 g of ammonium metavanadate and 37.50 g of antimony trioxide. The activity of the catalysts is controlled by variation of the cesium and phosphorus contents.

U.S. Pat. No. 4,356,112 states that the concomitant use of antimony improves the thermal stability and selectivity of catalysts for preparing phthalic anhydride. The best phthalic anhydride yields are obtained using a two-zone arrangement having a catalyst of the composition $V_2O_5:TiO_2:Nb_2O_5:P_2O_5:Cs_2O:Sb_2O_3=3:97:0.5:0.2:0.4:2.5$ in the first zone and one having the composition $V_2O_5:TiO_2:Nb_2O_5:P_2O_5:Cs_2O:Sb_2O_3=3:97:0.5:0.2:0.4:1.0$ in the second zone.

DE 198 39 001 teaches the use of coated catalysts for the gas-phase oxidation of hydrocarbons which comprise vanadium oxide, titanium dioxide and antimony oxide and in which two or more layers of catalytically active compositions are applied to a support, with the outer layer having a reduced antimony content.

EP-A 0 522 871 describes a catalyst for preparing phthalic anhydride by gas-phase oxidation, which is prepared using a pentavalent antimony compound as antimony source. The catalysts disclosed have a $V_2O_5:Sb_2O_3$ ratio of 2:2.0 or a $V_2O_5:Sb_2O_5$ ratio of 2:2.5.

As the catalyst in the first zone ages, its activity and thus its contribution to the total conversion in the reaction decreases. A higher proportion of unreacted hydrocarbons or partially oxidized intermediates goes through to the subsequent catalyst zones. The reaction increasingly moves to the subsequent catalyst zones which have a higher activity but a lower selectivity. Overall, the yield of desired product therefore decreases with increasing time of operation.

It is an object of the present invention to provide a process which allows the desired oxidation products to be obtained in high yield over a prolonged period of time.

We have found that this object is achieved by a process for preparing aldehydes, carboxylic acids and/or carboxylic anhydrides, in which a gaseous stream comprising an aromatic hydrocarbon and a gas comprising molecular oxygen is passed at elevated temperature over a bed of a first catalyst and a bed which is made up of a second catalyst having a higher activity than the first catalyst and is located downstream of the first catalyst in the flow direction of the gaseous stream, wherein the catalytically active composition of the first catalyst comprises at least vanadium oxide, titanium dioxide and antimony oxide and the ratio of vanadium, calculated as $V_2O_5$, to antimony, calculated as $Sb_2O_3$, in the first catalyst is from 3.5:1 to 5:1, preferably from 3.8:1 to 4.5:1.

It has been found that a lower ratio of vanadium to antimony than that indicated for the first catalyst leads to rapid aging of the catalyst and to the reaction being shifted into the downstream catalyst zones. A higher ratio than that indicated leads, particularly at high hydrocarbon loadings in the gas stream, to an unsatisfactory total yield.

The catalytically active composition of the second catalyst preferably also comprises at least vanadium oxide, titanium dioxide and antimony oxide and the ratio of vanadium, calculated as $V_2O_5$, to antimony, calculated as $Sb_2O_3$, in the second catalyst is, in particular, less than or equal to the corresponding ratio in the first catalyst.

Preference is given to a process in which the gaseous stream is additionally passed over a bed of a third and if desired fourth catalyst located downstream of the second catalyst. In general, the catalytically active composition of the third and fourth catalyst also comprises vanadium oxide and titanium dioxide.

The activity of the catalysts increases stepwise in the flow direction of the gas stream. Measures for controlling the activity of gas-phase oxidation catalysts based on vanadium oxide and titanium dioxide are known per se to those skilled in the art.

Thus, oxidic compounds which act as promoters and thus influence the activity and selectivity of the catalyst, for example by reducing or increasing its activity, may be present in the catalytically active composition.

Examples of activity-reducing promoters are the alkali metal oxides, in particular cesium oxide, lithium oxide, potassium oxide and rubidium oxide, thallium(I) oxide, aluminum oxide, zirconium oxide, iron oxide, nickel oxide, cobalt oxide, manganese oxide, tin oxide, silver oxide, copper oxide, chromium oxide, molybdenum oxide, tungsten oxide, iridium oxide, tantalum oxide, niobium oxide, arsenic oxide, antimony oxide, cerium oxide. Among this group, cesium is generally used as promoter. Possible sources of these elements are the oxides or hydroxides or salts which can be converted thermally into oxides, e.g.

carboxylates, in particular acetates, malonates or oxalates, carbonates, hydrogencarbonates or nitrates.

Suitable activity-increasing additives are, in particular, oxidic phosphorus compounds, in particular phosphorus pentoxide. Possible phosphorus sources are, in particular, phosphoric acid, phosphorous acid, hypophosphorous acid, ammonium phosphate or phosphoric esters and especially ammonium dihydrogenphosphate.

A further possible way of increasing the activity is to vary the proportion by weight of active composition in the total catalyst, with higher contents of active composition resulting in a higher activity and vice versa.

The titanium dioxide is usually employed in the anatase form. Its BET surface area is generally from 5 to 50 $m^2/g$, preferably from 8 to 28 $m^2/g$. The titanium dioxide used in at least one catalyst zone preferably comprises a mixture of titanium dioxides of differing BET surface areas. This mixture of titanium dioxide types comprises, for example, a low surface area titanium dioxide having a BET surface area of advantageously from 5 to 15 $m^2/g$, in particular from 5 to 10 $m^2/g$, and a higher surface area titanium dioxide having a BET surface area of advantageously from 10 to 70 $m^2/g$, in particular from 15 to 50 $m^2/g$. In particular, the titanium dioxide used consists of the two types of titanium dioxide mentioned. Such mixtures in which low surface area $TiO_2$ is present have the advantage that the BET surface area does not change over the life of the catalyst. This ensures a high stability of the activity, i.e. a longer catalyst life.

Particularly useful vanadium sources are vanadium pentoxide and ammonium metavanadate.

Suitable antimony sources are various antimony oxides, in particular antimony trioxide. Use is generally made of antimony trioxide having a mean particle size (maximum of the particle size distribution) of from 0.1 to 10 μm. The source of antimony oxide used for the first catalyst is particularly preferably particulate antimony trioxide having a mean particle size of from 0.5 to 5 μm, in particular from 1 to 4 μm. The use of an antimony trioxide of the particle size indicated leads to a significant improvement in the activity and selectivity of the first catalyst.

The catalysts used in the process of the present invention are generally coated catalysts in which the catalytically active composition is applied in the form of a shell to an inert support. The thickness of the coating of catalytically active composition is generally from 0.02 to 0.2 mm, preferably from 0.05 to 0.1 mm. In general, the layer of catalytically active composition applied in the form of a shell to the catalysts has an essentially homogeneous chemical composition.

As inert support material, it is possible to use virtually all support materials of the prior art which are advantageously used in the production of coated catalysts for the oxidation of aromatic hydrocarbons to aldehydes, carboxylic acids and/or carboxylic anhydrides, for example silica ($SiO_2$), porcelain, magnesium oxide, tin dioxide, silicon carbide, rutile, alumina ($Al_2O_3$), aluminum silicate, steatite (magnesium silicate), zirconium silicate, cerium silicate or mixtures of these support materials. The support material is generally nonporous. Advantageous support materials deserving of special mention are, in particular, steatite and silicon carbide. The shape of the support material is generally not critical for the precatalysts and coated catalysts used according to the present invention. For example, it is possible to use catalyst supports in the form of spheres, rings, pellets, spirals, tubes, extrudates or granules. The dimensions of these catalyst supports correspond to those of catalyst supports customarily used for producing coated catalysts for the gas-phase partial oxidation of aromatic hydrocarbons. Preference is given to using steatite in the form of spheres having a diameter of from 3 to 6 mm or rings having an external diameter of from 5 to 9 mm and a length of from 4 to 7 mm.

The individual layers of the coated catalyst can be applied by any methods known per se, e.g. by spraying solutions or suspensions onto the supports in a coating drum or coating with a solution or suspension in a fluidized bed. Organic binders, preferably copolymers, advantageously in the form of an aqueous dispersion, of vinyl acetate-vinyl laurate, vinyl acetate-acrylate, styrene-acrylate, vinyl acetate-maleate, vinyl acetate-ethylene, and hydroxyethylcellulose can be added to the catalytically active composition. It is advantageous to use amounts of binder of from 3 to 20% by weight, based on the solids content of the solution of the constituents of the active composition. If the catalytically active composition is applied to the support without organic binders, coating temperatures above 150° C. are advantageous. When the abovementioned binders are added, useable coating temperatures are, depending on the binder employed, in the range from 50 to 450° C. The binders applied burn out within a short time after installation of the catalyst in the reactor and start-up of the reactor. Furthermore, the addition of binder has the advantage that the active composition adheres well to the support, so that transport and installation of the catalyst are made easier.

In a preferred embodiment of the process of the present invention with three catalyst zones, the catalysts have the following composition (where the first zone is the zone located farthest upstream in the flow direction of the gas stream):

for the first zone:
from 7 to 10% by weight of active composition, based on the total catalyst, where this active composition comprises:
from 6 to 11% by weight of vanadium pentoxide,
from 1.2 to 3% by weight of antimony trioxide,
from 0.1 to 1% by weight of an alkali (calculated as alkali metal), in particular cesium oxide,
and the balance to 100% by weight of titanium dioxide, preferably in the anatase modification, having a BET surface area of from 5 to 30 $m^2/g$;

for the second zone:
from 7 to 12% by weight of active composition, based on the total catalyst, where this active composition comprises:
from 5 to 13% by weight of vanadium pentoxide,
from 0 to 3% by weight of antimony trioxide,
from 0 to 0.4% by weight of an alkali (calculated as alkali metal), in particular cesium oxide,
from 0 to 0.4% by weight of phosphorus pentoxide (calculated as P)
and the balance to 100% by weight of titanium dioxide, preferably in the anatase modification, having a BET surface area of from 10 to 40 $m^2/g$;

for the third zone:
from 8 to 12% by weight of active composition, based on the total catalyst, where this active composition comprises:
from 5 to 30% by weight of vanadium pentoxide,
from 0 to 3% by weight of antimony trioxide,
from 0 to 0.3% by weight of an alkali (calculated as alkali metal), in particular cesium oxide,
from 0.05 to 0.4% by weight of phosphorus pentoxide (calculated as P)
and the balance to 100% by weight of titanium dioxide, preferably in the anatase modification, having a BET surface area of from 15 to 50 $m^2/g$.

The ratio of the volumes occupied by the first, second and third zones is preferably 120-200:50-100:50-100.

In a preferred embodiment of the process of the present invention with four catalyst zones, the catalysts have the following composition (where the first zone is the zone located farthest upstream in the flow direction of the gas stream):

for the first zone:
from 7 to 10% by weight of active composition, based on the total catalyst, where this active composition comprises:
from 6 to 11% by weight of vanadium pentoxide,
from 1.2 to 3% by weight of antimony trioxide,
from 0.1 to 1% by weight of an alkali (calculated as alkali metal), in particular cesium oxide,
and the balance to 100% by weight of titanium dioxide, preferably in the anatase modification, having a BET surface area of from 5 to 30 m$^2$/g;

for the second zone:
from 7 to 10% by weight of active composition, based on the total catalyst, where this active composition comprises:
from 4 to 15% by weight of vanadium pentoxide,
from 0 to 3% by weight of antimony trioxide,
from 0.1 to 1% by weight of an alkali (calculated as alkali metal), in particular cesium oxide,
from 0 to 0.4% by weight of phosphorus pentoxide (calculated as P)
and the balance to 100% by weight of titanium dioxide, preferably in the anatase modification, having a BET surface area of from 10 to 35 m$^2$/g;

for the third zone:
from 7 to 10% by weight of active composition, based on the total catalyst, where this active composition comprises:
from 5 to 13% by weight of vanadium pentoxide,
from 0 to 3% by weight of antimony trioxide,
from 0 to 0.4% by weight of an alkali (calculated as alkali metal), in particular cesium oxide,
from 0 to 0.4% by weight of phosphorus pentoxide (calculated as P)
and the balance to 100% by weight of titanium dioxide, preferably in the anatase modification, having a BET surface area of from 15 to 40 m$^2$/g;

for the fourth zone:
from 8 to 12% by weight of active composition, based on the total catalyst, where this active composition comprises:
from 10 to 30% by weight of vanadium pentoxide,
from 0 to 3% by weight of antimony trioxide,
from 0.05 to 0.4% by weight of phosphorus pentoxide (calculated as P)
and the balance to 100% by weight of titanium dioxide, preferably in the anatase modification, having a BET surface area of from 15 to 50 m$^2$/g.

The ratio of the volumes occupied by the first, second, third and fourth zones is preferably 80-160:20-60:30-100:40-90.

If desired, a downstream finishing reactor as described, for example, in DE-A 198 07 018 or DE-A 20 05 969 A can also be provided for the preparation of phthalic anhydride. The catalyst used in this reactor is preferably a catalyst having an even higher activity than the catalyst of the last zone.

The process of the present invention is suitable in general for the gas-phase oxidation of aromatic $C_6$-$C_{10}$-hydrocarbons such as benzene, the xylenes, toluene, naphthalene or durene (1,2,4,5-tetramethylbenzene) to carboxylic acids and/or carboxylic anhydrides, e.g. maleic anhydride, phthalic anhydride, benzoic acid and/or pyromellitic dianhydride. The process is particularly useful for preparing phthalic anhydride from o-xylene and/or naphthalene.

For this purpose, the catalysts are introduced into reaction tubes which are thermostated from the outside to the reaction temperature, for example by means of salt melts, and the reaction gas is passed over the catalyst bed prepared in this way at temperatures of generally from 300 to 450° C., preferably from 320 to 420° C. and particularly preferably from 340 to 400° C., and a gauge pressure of generally from 0.1 to 2.5 bar, preferably from 0.3 to 1.5 bar, and a space velocity of generally from 750 to 5000 h$^{-1}$.

The reaction gas passed over the catalyst is generally produced by mixing a gas which comprises molecular oxygen and may further comprise appropriate reaction moderators and/or diluents such as steam, carbon dioxide and/or nitrogen with the aromatic hydrocarbon to be oxidized, where the gas comprising molecular oxygen generally comprises from 1 to 100 mol %, preferably from 2 to 50 mol % and particularly preferably from 10 to 30 mol %, of oxygen, from 0 to 30 mol %, preferably from 0 to 10 mol %, of water vapor and from 0 to 50 mol %, preferably from 0 to 1 mol %, of carbon dioxide, balance nitrogen. To produce the reaction gas, the gas comprising molecular oxygen is generally mixed with from 30 g to 150 g per standard m$^3$ of gas, preferably from 60 to 120 g per standard m$^3$, of the aromatic hydrocarbon to be oxidized.

It is possible for two or more regions, preferably two regions, of the catalyst bed present in the reaction tube to be thermostated to different reaction temperatures, which can be achieved using, for example, reactors having separate salt baths. Alternatively, the gas-phase oxidation can also be carried out at a single reaction temperature without division into temperature regions.

The invention is illustrated by the accompanying FIGURE and the following examples. In the examples, the catalyst zone located farthest upstream in the flow direction of the gas stream is designated as the upper zone, and the catalyst zone located farthest downstream is designated as the bottom zone. One or more middle zones may be present between these. The particle size of the antimony trioxide was measured by means of a Fritsch particle sizer "Analysette 22" in the measuring range from 0.3 to 300 µm at a resolution of 62 channels. The measurement time was 2 scans. Evaluation was carried out by the Frauenhofer method.

FIG. 1 shows a plot of stability index versus time for the catalysts for examples 1 and 2; the stability index indicates the quantity of heat generated in the catalyst zones following the first zone relative to the total quantity of heat.

EXAMPLES

Catalyst Bed Example 1 (According to the Present Invention)

Upper Zone:
29.8 g of anatase (BET surface area=9 m$^2$/g), 69.6 g of anatase (BET surface area=20 m$^2$/g), 7.1 g of $V_2O_5$, 1.8 g of $Sb_2O_3$ (maximum of the particle size distribution at 2.36 µm) and 0.46 g of $Cs_2CO_3$ were suspended in 550 ml of deionized water and stirred for 15 hours. 50 g of an aqueous dispersion (50% by weight) derived from vinyl acetate and vinyl laurate were subsequently added to this suspension. The suspension was subsequently applied by spraying to 1200 g of shaped steatite bodies (magnesium silicate) in the form of rings (7×7×4 mm, external diameter×length×internal diameter, ED×L×ID). The weight of the coating of active composition applied was 8.0% of the total weight of the finished catalyst.

The catalytically active composition applied in this way comprised, after calcination at 400° C. for 4 hours, 6.8% by weight of $V_2O_5$, 1.7% by weight of $Sb_2O_3$, 0.33% by weight of Cs. ($V_2O_5$:$Sb_2O_3$ ratio=4).

Middle Zone:

26.6 g of anatase (BET surface area=9 $m^2$/g), 79.9 g of anatase (BET surface area=20 $m^2$/g), 7.55 g of $V_2O_5$, 1.89 g of $Sb_2O_3$ and 0.14 g of $Cs_2CO_3$ were suspended in 550 ml of deionized water and stirred for 15 hours. 55 g of an aqueous dispersion (50% by weight) derived from vinyl acetate and vinyl laurate were subsequently added to this suspension. The suspension was subsequently applied by spraying to 1200 g of shaped steatite bodies (magnesium silicate) in the form of rings (7×7×4 mm, ED×L×ID). The weight of the coating of active composition applied was 8.7% of the total weight of the finished catalyst.

The catalytically active composition applied in this way comprised, after calcination at 400° C. for 4 hours, 6.4% by weight of $V_2O_5$, 1.7% by weight of $Sb_2O_3$, 0.09% by weight of Cs.

Bottom Zone:

17.4 g of anatase (BET surface area=9 $m^2$/g), 69.6 g of anatase (BET surface area=27 $m^2$/g), 21.7 g of $V_2O_5$ and 1.5 g of $NH_4H_2PO_4$ were suspended in 550 ml of deionized water and stirred for 15 hours. 55 g of an aqueous dispersion (50% by weight) derived from vinyl acetate and vinyl laurate were subsequently added to this suspension. The suspension was subsequently applied by spraying to 1200 g of shaped steatite bodies (magnesium silicate) in the form of rings (7×7×4 mm, ED×L×ID). The weight of the coating of active composition applied was 9.0% of the total weight of the finished catalyst.

The catalytically active composition applied in this way comprised, after calcination at 400° C. for 4 hours, 20.0% by weight of $V_2O_5$, 0.37% by weight of P.

Example 2 (Comparison)

Upper Zone:

29.8 g of anatase (BET surface area=9 $m^2$/g), 69.6 g of anatase (BET surface area=20 $m^2$/g), 7.1 9 of $V_2O_5$, 2.3 g of $Sb_2O_3$ (maximum of the particle size distribution at 2.36 μm) and 0.46 g of $Cs_2CO_3$ were suspended in 550 ml of deionized water and stirred for 15 hours. 50 g of an aqueous dispersion (50% by weight) derived from vinyl acetate and vinyl laurate were subsequently added to this suspension. The suspension was subsequently applied by spraying to 1200 g of shaped steatite bodies (magnesium silicate) in the form of rings (7×7×4 mm, ED×L×ID). The weight of the coating of active composition applied was 8.0% of the total weight of the finished catalyst.

The catalytically active composition applied in this way comprised, after calcination at 400° C. for 4 hours, 6.8% by weight of $V_2O_5$, 2.2% by weight of $Sb_2O_3$, 0.33% by weight of Cs. ($V_2O_5$:$Sb_2O_3$ ratio=3).

Middle Zone:

26.6 g of anatase (BET surface area=9 $m^2$/g), 79.9 g of anatase (BET surface area=20 $m^2$/g), 7.55 g of $V_2O_5$, 1.89 g of $Sb_2O_3$ and 0.14 g of $Cs_2CO_3$ were suspended in 550 ml of deionized water and stirred for 15 hours. 55 g of an aqueous dispersion (50% by weight) derived from vinyl acetate and vinyl laurate were subsequently added to this suspension. The suspension was subsequently applied by spraying to 1200 g of shaped steatite bodies (magnesium silicate) in the form of rings (7×7×4 mm, ED×L×ID). The weight of the coating of active composition applied was 8.7% of the total weight of the finished catalyst.

The catalytically active composition applied in this way comprised, after calcination at 400° C. for 4 hours, 6.4% by weight of $V_2O_5$, 1.7% by weight of $Sb_2O_3$, 0.09% by weight of Cs.

Bottom Zone:

17.4 g of anatase (BET surface area=9 $m^2$/g), 69.6 g of anatase (BET surface area=27 $m^2$/g), 21.7 g of $V_2O_5$ and 1.5 g of $NH_4H_2PO_4$ were suspended in 550 ml of deionized water and stirred for 15 hours. 55 g of an aqueous dispersion (50% by weight) derived from vinyl acetate and vinyl laurate were subsequently added to this suspension. The suspension was subsequently applied by spraying to 1200 g of shaped steatite bodies (magnesium silicate) in the form of rings (7×7×4 mm, ED×L×ID). The weight of the coating of active composition applied was 9.0% of the total weight of the finished catalyst.

The catalytically active composition applied in this way comprised, after calcination at 400° C. for 4 hours, 20.0% by weight of $V_2O_5$, 0.37% by weight of P.

Catalyst Bed Example 3 (According to the Present Invention)

Upper Zone:

29.3 g of anatase (BET surface area=9 $m^2$/g), 69.8 g of anatase (BET surface area=20 $m^2$/g), 7.8 g of $V_2O_5$, 1.9 g of $Sb_2O_3$ (maximum of the particle size distribution at 2.36 μm) and 0.49 g of $Cs_2CO_3$ were suspended in 550 ml of deionized water and stirred for 15 hours. 50 g of an aqueous dispersion (50% by weight) derived from vinyl acetate and vinyl laurate were subsequently added to this suspension. The suspension was subsequently applied by spraying to 1200 g of shaped steatite bodies (magnesium silicate) in the form of rings (7×7×4 mm, ED×L×ID). The weight of the coating of active composition applied was 8.0% of the total weight of the finished catalyst.

The catalytically active composition applied in this way comprised, after calcination at 400° C. for 4 hours, 7.1% by weight of $V_2O_5$, 1.8% by weight of $Sb_2O_3$, 0.36% by weight of Cs. ($V_2O_5$:$Sb_2O_3$ ratio=4).

Middle Zone 1:

24.6 g of anatase (BET surface area=9 $m^2$/g), 74.5 g of anatase (BET surface area=27 $m^2$/g), 7.8 g of $V_2O_5$, 2.6 g of $Sb_2O_3$ and 0.35 g of $Cs_2CO_3$ were suspended in 550 ml of deionized water and stirred for 15 hours. 50 g of an aqueous dispersion (50% by weight) derived from vinyl acetate and vinyl laurate were subsequently added to this suspension. The suspension was subsequently applied by spraying to 1200 g of shaped steatite bodies (magnesium silicate) in the form of rings (7×7×4 mm, ED×L×ID). The weight of the coating of active composition applied was 8.0% of the total weight of the finished catalyst.

The catalytically active composition applied in this way comprised, after calcination at 400° C. for 4 hours, 7.1% by weight of $V_2O_5$, 2.4% by weight of $Sb_2O_3$, 0.26% by weight of Cs.

Middle Zone 2:

24.8 g of anatase (BET surface area=9 $m^2$/g), 74.5 g of anatase (BET surface area=27 $m^2$/g), 7.8 g of $V_2O_5$, 2.6 g of $Sb_2O_3$ and 0.13 g of $Cs_2CO_3$ were suspended in 550 ml of deionized water and stirred for 15 hours. 50 g of an aqueous dispersion (50% by weight) derived from vinyl acetate and vinyl laurate were subsequently added to this suspension. The suspension was subsequently applied by spraying to 1200 g of shaped steatite bodies (magnesium silicate) in the form of rings (7×7×4 mm, ED×L×ID). The weight of the coating of active composition applied was 8.0% of the total weight of the finished catalyst.

The catalytically active composition applied in this way comprised, after calcination at 400° C. for 4 hours, 7.1% by weight of $V_2O_5$, 2.4% by weight of $Sb_2O_3$, 0.10% by weight of Cs.

Bottom Zone:

17.2 g of anatase (BET surface area=9 m²/g), 69.1 g of anatase (BET surface area=27 m²/g), 21.9 g of $V_2O_5$, and 1.5 g of $NH_4H_2PO_4$ were suspended in 550 ml of deionized water and stirred for 15 hours. 55 g of an aqueous dispersion (50% by weight) derived from vinyl acetate and vinyl laurate were subsequently added to this suspension. The suspension was subsequently applied by spraying to 1200 g of shaped steatite bodies (magnesium silicate) in the form of rings (7×7×4 mm, ED×L×ID). The weight of the coating of active composition applied was 8.0% of the total weight of the finished catalyst.

The catalytically active composition applied in this way comprised, after calcination at 400° C. for 4 hours, 20.0% by weight of $V_2O_5$, 0.38% by weight of P.

Catalyst Bed Example 4 (Comparison)

Upper Zone:

29.3 g of anatase (BET surface area=9 m²/g), 69.8 g of anatase (BET surface area=20 m²/g), 7.8 g of $V_2O_5$, 2.6 g of $Sb_2O_3$ (maximum of the particle size distribution at 2.36 µm) and 0.49 g of $Cs_2CO_3$ were suspended in 550 ml of deionized water and stirred for 15 hours. 50 g of an aqueous dispersion (50% by weight) derived from vinyl acetate and vinyl laurate were subsequently added to this suspension. The suspension was subsequently applied by spraying to 1200 g of shaped steatite bodies (magnesium silicate) in the form of rings (7×7×4 mm, ED×L×ID). The weight of the coating of active composition applied was 8.0% of the total weight of the finished catalyst.

The catalytically active composition applied in this way comprised, after calcination at 400° C. for 4 hours, 7.1% by weight of $V_2O_5$, 2.4% by weight of $Sb_2O_3$, 0.36% by weight of Cs. ($V_2O_5$:$Sb_2O_3$ ratio=3).

Middle Zone 1:

24.6 g of anatase (BET surface area=9 m²/g), 74.5 g of anatase (BET surface area=27 m²/g), 7.8 g of $V_2O_5$, 2.6 g of $Sb_2O_3$ and 0.35 g of $Cs_2CO_3$ were suspended in 550 ml of deionized water and stirred for 15 hours. 50 g of an aqueous dispersion (50% by weight) derived from vinyl acetate and vinyl laurate were subsequently added to this suspension. The suspension was subsequently applied by spraying to 1200 g of shaped steatite bodies (magnesium silicate) in the form of rings (7×7×4 mm, ED×L×ID). The weight of the coating of active composition applied was 8.0% of the total weight of the finished catalyst.

The catalytically active composition applied in this way comprised, after calcination at 400° C. for 4 hours, 7.1% by weight of $V_2O_5$, 2.4% by weight of $Sb_2O_3$, 0.26% by weight of Cs.

Middle Zone 2:

24.8 g of anatase (BET surface area=9 m²/g), 74.5 g of anatase (BET surface area=27 m²/g), 7.8 g of $V_2O_5$, 2.6 g of $Sb_2O_3$ and 0.13 g of $Cs_2CO_3$ were suspended in 550 ml of deionized water and stirred for 15 hours. 50 g of an aqueous dispersion (50% by weight) derived from vinyl acetate and vinyl laurate were subsequently added to this suspension. The suspension was subsequently applied by spraying to 1200 g of shaped steatite bodies (magnesium silicate) in the form of rings (7×7×4 mm, ED×L×ID). The weight of the coating of active composition applied was 8.0% of the total weight of the finished catalyst.

The catalytically active composition applied in this way comprised, after calcination at 400° C. for 4 hours, 7.1% by weight of $V_2O_5$, 2.4% by weight of $Sb_2O_3$, 0.10% by weight of Cs.

Bottom Zone:

17.2 g of anatase (BET surface area=9 m²/g), 69.1 g of anatase (BET surface area=27 m²/g), 21.9 g of $V_2O_5$ and 1.5 g of $NH_4H_2PO_4$ were suspended in 550 ml of deionized water and stirred for 15 hours. 55 g of an aqueous dispersion (50% by weight) derived from vinyl acetate and vinyl laurate were subsequently added to this suspension. The suspension was subsequently applied by spraying to 1200 g of shaped steatite bodies (magnesium silicate) in the form of rings (7×7×4 mm, ED×L×ID). The weight of the coating of active composition applied was 8.0% of the total weight of the finished catalyst.

The catalytically active composition applied in this way comprised, after calcination at 400° C. for 4 hours, 20.0% by weight of $V_2O_5$, 0.38% by weight of P.

Catalyst Bed Example 5

Upper Zone:

29.3 g of anatase (BET surface area=9 m²/g), 69.8 g of anatase (BET surface area=20 m²/g), 7.8 g of $V_2O_5$, 1.9 g of $Sb_2O_3$ (maximum of the particle size distribution at 7.42 µm) and 0.49 g of $Cs_2CO_3$ were suspended in 550 ml of deionized water and stirred for 15 hours. 50 g of an aqueous dispersion (50% by weight) derived from vinyl acetate and vinyl laurate were subsequently added to this suspension. The suspension was subsequently applied by spraying to 1200 g of shaped steatite bodies (magnesium silicate) in the form of rings (7×7×4 mm, ED×L×ID). The weight of the coating of active composition applied was 8.0% of the total weight of the finished catalyst.

The catalytically active composition applied in this way comprised, after calcination at 400° C. for 4 hours, 7.1% by weight of $V_2O_5$, 1.8% by weight of $Sb_2O_3$, 0.36% by weight of Cs.

Middle Zone 1:

24.6 g of anatase (BET surface area=9 m²/g), 74.5 g of anatase (BET surface area=27 m²/g), 7.8 g of $V_2O_5$, 2.6 g of $Sb_2O_3$ and 0.35 g of $Cs_2CO_3$ were suspended in 550 ml of deionized water and stirred for 15 hours. 50 g of an aqueous dispersion (50% by weight) derived from vinyl acetate and vinyl laurate were subsequently added to this suspension. The suspension was subsequently applied by spraying to 1200 g of shaped steatite bodies (magnesium silicate) in the form of rings (7×7×4 mm, ED×L×ID). The weight of the coating of active composition applied was 8.0% of the total weight of the finished catalyst.

The catalytically active composition applied in this way comprised, after calcination at 400° C. for 4 hours, 7.1% by weight of $V_2O_5$, 2.4% by weight of $Sb_2O_3$, 0.26% by weight of Cs.

Middle Zone 2:

24.8 g of anatase (BET surface area=9 m²/g), 74.5 g of anatase (BET surface area=27 m²/g), 7.8 g of $V_2O_5$, 2.6 g of $Sb_2O_3$ and 0.13 g of $Cs_2CO_3$ were suspended in 550 ml of deionized water and stirred for 15 hours. 50 g of an aqueous dispersion (50% by weight) derived from vinyl acetate and vinyl laurate were subsequently added to this suspension. The suspension was subsequently applied by spraying to 1200 g of shaped steatite bodies (magnesium silicate) in the form of rings (7×7×4 mm, ED×L×ID). The weight of the coating of active composition applied was 8.0% of the total weight of the finished catalyst.

The catalytically active composition applied in this way comprised, after calcination at 400° C. for 4 hours, 7.1% by weight of $V_2O_5$, 2.4% by weight of $Sb_2O_3$, 0.10% by weight of Cs.

Bottom Zone:

17.2 g of anatase (BET surface area=9 m²/g), 69.1 g of anatase (BET surface area=27 m²/g), 21.9 g of $V_2O_5$, and 1.5 g of $NH_4H_2PO_4$ were suspended in 550 ml of deionized water and stirred for 15 hours. 55 g of an aqueous dispersion (50% by weight) derived from vinyl acetate and vinyl laurate were subsequently added to this suspension. The suspension was subsequently applied by spraying to 1200 g of shaped steatite bodies (magnesium silicate) in the form of rings (7×7×4 mm, ED×L×ID). The weight of the coating of active composition applied was 8.0% of the total weight of the finished catalyst.

The catalytically active composition applied in this way comprised, after calcination at 400° C. for 4 hours, 20.0% by weight of $V_2O_5$, 0.38% by weight of P.

Catalytic Tests:

The tests were carried out in a reactor which had a length of 3.85 m and an internal diameter of 25 mm and was cooled by means of a salt bath and into which the catalysts of examples 1 to 5 had been introduced starting with the bottom zone catalyst. To record a temperature profile, the reactor was equipped with a thermocouple which could be moved over the entire length of the reactor. The thermocouple was located in a sheath having an external diameter of 2 mm. 4.0 standard m³/h of air laden with 80 or 100 g/standard m³ of o-xylene (purity at least 98.5%) were passed through the tube from the top downward. The results summarized in the table below were obtained ("PA yield" is parts by mass of phthalic anhydride obtained per 100 parts by mass of pure o-xylene).

Determination of the Stability Index

The stability index S(stab) indicates the quantity of heat generated in the catalyst zones following the first zone relative to the total quantity of heat. It is defined by the following equation:

$$S(stab)=A(2+3+\ldots)/A(1+2+3+\ldots)$$

where $A(1+2+3+\ldots)$ is the integrated area under the temperature-bed height curve of all catalysts zones and $A(2+3+\ldots)$ is the corresponding area for the catalyst zones following the first zone. The temperature-bed height curve can easily be obtained by plotting the temperature determined by means of the thermocouple against the position of the thermocouple.

FIG. 1 shows a comparison of the plots of S(stab) versus time for the catalysts of examples 1 and 2. It can be seen that smaller quantities of heat are evolved in the second and third catalyst zones over the period of time in question in example 1 according to the present invention.

TABLE 1

|  | Example 1 | Example 2 | Example 3 | Example 4 | Example 5 |
| --- | --- | --- | --- | --- | --- |
| Bed length [cm] | 170, 70, 70 | 170, 70, 70 | 130, 50, 80, 60 | 130, 50, 80, 60 | 130, 50, 80, 60 |
| Loading [g/standard m³] | 80 | 80 | 100 | 100 | 100 |
| Time of operation [d] | 60 | 60 | 43 | 44 | 42 |
| Salt bath temp. [° C.] | 360 | 361 | 354 | 353 | 350 |
| Hot spot temp. in upper zone [° C.] | 440 | 435 | 440 | 437 | 444 |
| Phthalide [% by weight] | 0.01 | 0.04 | 0.02 | 0.04 | 0.07 |
| PA yield | 114.2 | 112.4 | 113.5 | 113.0 | 112.7 |

Comparison of example 1 with example 2 and example 3 with example 4 shows that higher yields are obtained when using a catalyst having the $V_2O_5$:$Sb_2O_3$ ratio according to the present invention in the first zone. Comparison of example 3 with example 5 shows the influence of the particle size of the antimony trioxide used for producing the first catalyst.

The invention claimed is:

1. A process for preparing phthalic anhydride, in which a gaseous stream comprising an aromatic hydrocarbon, selected from o-xylene and/or naphthalene and a gas comprising molecular oxygen is passed at a temperature of from 300 to 450° C. over a bed of a first catalyst and a bed which is made up of a second catalyst having a higher activity than the first catalyst and is located downstream of the first catalyst in the flow direction of the gaseous stream, wherein the catalytically active composition of the first catalyst comprises at least vanadium oxide, titanium dioxide and antimony oxide and the weight ratio of vanadium, calculated as $V_2O_5$, to antimony, calculated as $Sb_2O_3$, in the first catalyst is from 3.5:1 to 4.5:1 and wherein the catalytically active composition of the second catalyst comprises at least vanadium oxide, titanium dioxide and antimony oxide and the weight ratio of vanadium to antimony in the second catalyst is less than or equal to the corresponding weight ratio in the first catalyst.

2. A process as claimed in claim 1, wherein the ratio of vanadium to antimony in the first catalyst is from 3.8:1 to 4.5:1.

3. A process as claimed in claim 1, wherein the source of antimony oxide used for the first catalyst is particulate antimony trioxide having a mean particle size of from 0.5 to 5 μm.

4. A process as claimed in claim 1, wherein the gaseous stream is additionally passed over a bed of a third and, optionally, fourth catalyst located downstream of the second catalyst.

5. A process as claimed in claim 1, wherein the loading of the gaseous aromatic hydrocarbon is from 30 to 150 g per standard m$^3$ of gas.

6. A process as claimed in claim 2, wherein the source of antimony oxide used for the first catalyst is particulate antimony trioxide having a mean particle size of from 0.5 to 5 μm.

7. A process as claimed in claim 2, wherein the gaseous stream is additionally passed over a bed of a third and, optionally, fourth catalyst located downstream of the second catalyst.

8. A process as claimed in claim 3, wherein the gaseous stream is additionally passed over a bed of a third and, optionally, fourth catalyst located downstream of the second catalyst.

9. A process as claimed in claim 2, wherein the catalytically active composition of the second catalyst comprises at least vanadium oxide, titanium dioxide and antimony oxide and the ratio of vanadium to antimony in the second catalyst is less than or equal to the corresponding ratio in the first catalyst.

10. A process as claimed in claim 3, wherein the catalytically active composition of the second catalyst comprises at least vanadium oxide, titanium dioxide and antimony oxide and the ratio of vanadium to antimony in the second catalyst is less than or equal to the corresponding ratio in the first catalyst.

11. A process as claimed in claim 4, wherein the catalytically active composition of the second catalyst comprises at least vanadium oxide, titanium dioxide and antimony oxide and the ratio of vanadium to antimony in the second catalyst is less than or equal to the corresponding ratio in the first catalyst.

12. A process as claimed in claim 2, wherein the loading of the gaseous aromatic hydrocarbon is from 30 to 150 g per standard m$^3$ of gas.

13. A process as claimed in claim 3, wherein the loading of the gaseous aromatic hydrocarbon is from 30 to 150 g per standard m$^3$ of gas.

14. A process as claimed in claim 4, wherein the loading of the gaseous aromatic hydrocarbon is from 30 to 150 g per standard m$^3$ of gas.

15. A process as claimed in claim 6, wherein the loading of the gaseous aromatic hydrocarbon is from 30 to 150 g per standard m$^3$ of gas.

* * * * *